(12) United States Patent
Ma et al.

(10) Patent No.: US 8,779,167 B2
(45) Date of Patent: Jul. 15, 2014

(54) METHOD FOR PREPARING A STATIN COMPOUND BY LACTONIZATION

(75) Inventors: Deyin Ma, Chongqing (CN); Qingkai He, Chongqing (CN); Yunhui Zhang, Chongqing (CN)

(73) Assignees: Peking University Founder Group Co., Ltd., Beijing (CN); Southwest Synthetic Pharmaceutical Corp., Ltd., Chongqing (CN); PKU International Healthcare Group Co., Ltd., Beijing (CN)

( * ) Notice: Subject to any disclaimer, the term of this patent is extended or adjusted under 35 U.S.C. 154(b) by 0 days.

(21) Appl. No.: 13/510,701

(22) PCT Filed: Nov. 22, 2010

(86) PCT No.: PCT/CN2010/078949
§ 371 (c)(1),
(2), (4) Date: Aug. 3, 2012

(87) PCT Pub. No.: WO2011/060742
PCT Pub. Date: May 26, 2011

(65) Prior Publication Data
US 2012/0296099 A1 Nov. 22, 2012

(30) Foreign Application Priority Data
Nov. 20, 2009 (CN) .......................... 2009 1 0191545

(51) Int. Cl.
*C07D 309/30* (2006.01)
(52) U.S. Cl.
USPC ......................................................... 549/292
(58) Field of Classification Search
USPC ......................................................... 549/292
See application file for complete search history.

(56) References Cited

U.S. PATENT DOCUMENTS

| 4,444,784 A | 4/1984 | Hoffman et al. |
| 4,582,915 A | 4/1986 | Sleteinger et al. |
| 4,820,850 A | 4/1989 | Verhoeven et al. |
| 4,916,239 A | 4/1990 | Treiber |
| 6,307,066 B1 | 10/2001 | Murthy et al. |
| 6,562,984 B2 * | 5/2003 | Peters et al. .................. 549/292 |
| 6,649,775 B2 * | 11/2003 | Lee et al. ........................ 549/292 |
| 2002/0156298 A1 * | 10/2002 | McManus et al. ............ 549/292 |

FOREIGN PATENT DOCUMENTS

| CN | 1406938 A | 4/2003 |
| CN | 101704808 A | 5/2010 |
| EP | 1110959 | 6/2001 |
| EP | 1288212 | 3/2003 |
| WO | 02072566 | 9/2002 |

OTHER PUBLICATIONS

PCT/CN2010/078949 International Preliminary Report on Patentability with Written Opinion, issued May 22, 2011, 7 pages.
EP 10831157 Supplementary European Search Report, Mar. 7, 2013, 3 pages.

* cited by examiner

*Primary Examiner* — Nizal Chandrakumar
(74) *Attorney, Agent, or Firm* — Lathrop & Gage LLP

(57) ABSTRACT

A method for preparing a statin compound by lactonization is disclosed, which comprises the following step: lactonizing a compound of formula II into the compound of formula I in the presence of a strong acid catalyst and a dehydrant in a first solvent,

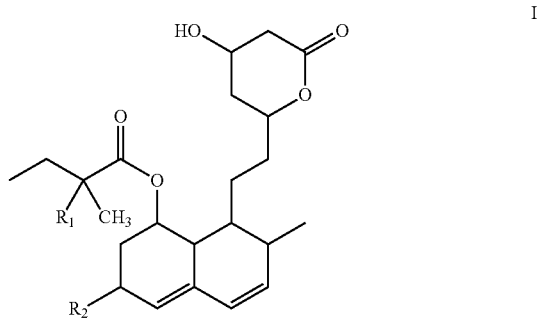

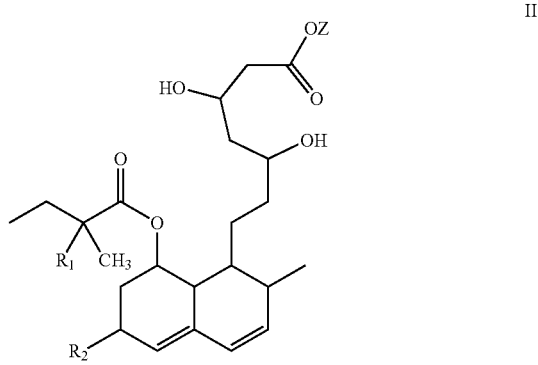

wherein Z represents H, ammonium, or a metal cations;
$R_1$ is H or $C_1$-$C_6$ alkyl, preferably H or $CH_3$,
$R_2$ is $CH_3$, OH, $CH_2OH$, $CH_2OC(O)R_3$, $CH_2OR_3$, or $COOR_4$, preferably $CH_3$ or OH,
$R_3$ and $R_4$ are independently selected from the group consisting of H and $C_1$-$C_6$ alkyl.

27 Claims, No Drawings

METHOD FOR PREPARING A STATIN COMPOUND BY LACTONIZATION

This application is a national phase application of PCT application PCT/CN2010/078949, which claims priority to Chinese Patent Application 200910191545.4, filed Nov. 20, 2009. The disclosures of the aforementioned applications are incorporated herein by reference.

FIELD OF THE INVENTION

The present invention relates to a method for preparing a statin compound, particularly to a method for preparing a statin compound by lactonization, and more particularly to a method for preparing simvastatin by lactonization.

BACKGROUND OF THE INVENTION

Hypercholesterolemia is considered to be the uppermost risk factor for ischemic cardiovascular diseases such as arteriosclerosis and coronary disease. Compounds such as mevastatin, lovastatin, pravastatin and simvastatin reduce biosynthesis of cholesterol in human by inhibiting the first rate-limiting enzyme, HMG-CoA reductase, in the biosynthesis of cholesterol, and are therefore widely used as agents for reducing cholesterol concentration in plasma. This class of compounds is referred to as statin compounds, which are present in the form of lactones as shown in formula I, or in the form of dihydroxy acids with open ring structures as shown in formula II.

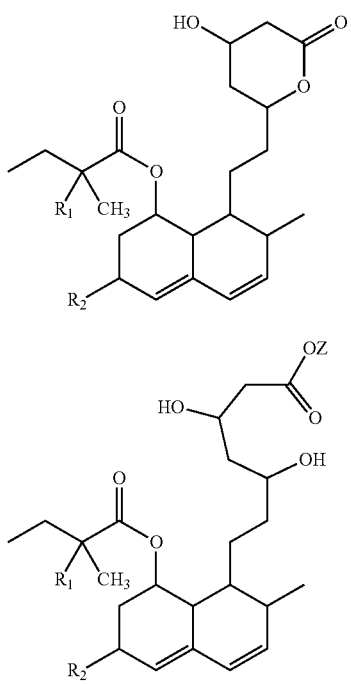

wherein Z represents H, ammonium, or a metal cation,
R$_1$ is H or CH$_3$,
R$_2$ is CH$_3$ or OH.

The statin compounds are generally administered to a patient in the form of lactones, and then hydrolysed to active metabolites in the form of dihydroxy acids. As a result, there exists a need for development of methods for preparing statin compounds by lactonization. Lactonization is an equilibrium process. In order to obtain a high yield of the lactones, particular methods have to be employed to shift the equilibrium to the lactone side of the equation:

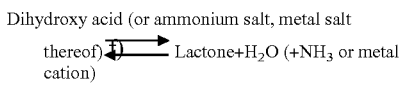

Dihydroxy acid (or ammonium salt, metal salt thereof) ⇌ Lactone+H$_2$O (+NH$_3$ or metal cation)

U.S. Pat. Nos. 4,444,784, 4,582,915, 4,820,850, U.S. Pat. No. 6,307,066B1, and U.S. Pat. No. 6,797,381B2 disclose that the equilibrium is shifted to the lactone side of the equation by azeotropic distillation or introducing an inert gas flow to the hot reaction solvent so as to remove water or ammonia.

All of the above methods have disadvantages, such as high reaction temperatures and long reaction times. Since dihydroxy acids are sensitive to heat, high temperature and longer reaction time will lead to formation of a dimer impurity resulting from a further esterification reaction between 3-hydroxyl group of the lactone and the free dihydroxy acids, and thus the overall output and purity of lactones are decreased. Since the acceptable impurity level of dimers should be less than 0.2%, the above methods are not beneficial to the preparation of statin compounds with high purity.

U.S. Pat. No. 4,916,239 discloses a method for converting a dihydroxy acid or salt thereof into a lactone in a water miscible solvent (especially acetic acid medium) by use of a strong acid catalyst. After a period of reaction time, an appropriate amount of water is added to the reaction mixture to isolate the insoluble lactone, thereby shifting the equilibrium to generate subsequent lactones. This method eliminates the need of high temperature, and decreases the amount of dimmer impurities. However, this method needs 1.2-1.5 moles of strong acid such as methanesulfonic acid, sulphuric acid and trifluoroacetic acid, and therefore needs a large amount of strong base for neutralization and tedious post-processing. As a result, the method is not suitable for industrial scale production and is harmful to the environment. In addition, completion of lactonization requires addition of extra water, which leads to a further crystallization on the formed crystal, and results in heterogeneity of lactone structure and lower purity. Meanwhile, too quick or premature addition of water and inappropriate amount of water lead to an incomplete reaction, lengthen reaction time and post-processing time to up to 9-12 hours, which decreases production efficiency.

U.S. Pat. No. 6,562,984 discloses that water generated during the lactonization reaction between the lactonization agent, methanesulfonic acid, and dihydroxy acid or a salt thereof is allowed to form a hydrated complex in the solvent CH$_2$Cl$_2$. Since the hydrated complex is substantially insoluble in the solvent, it can be removed by filtration. However, the method requires a strict anhydrous condition, the solvent CH$_2$Cl$_2$ requires anhydrous treatment prior to use, and the agent methanesulfonic acid should also be anhydrous. In addition, the reaction requires a CaCl$_2$ drying tube to isolate and absorb the moisture in the air, needs to be protected by introducing nitrogen gas, and is strict with reaction devices and operations. Moreover, the complex of by-product methanesulfonic ammonium generated after the reaction and water is relatively viscous, and is difficult to be filtrated, which have some effects on the environment and operations.

Therefore, there exists a need for novel methods for preparing statin compounds by lactonization.

SUMMARY OF THE INVENTION

In one aspect, the present invention provides a method for preparing a statin compound by lactonization, comprising lactonizing a compound of formula II into a compound of formula I in the presence of a strong acid catalyst and a dehydrant in a first solvent,

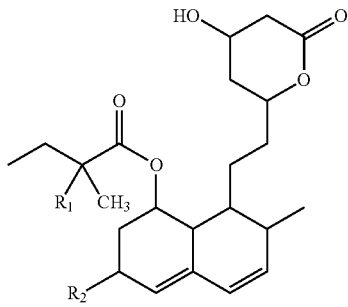

I

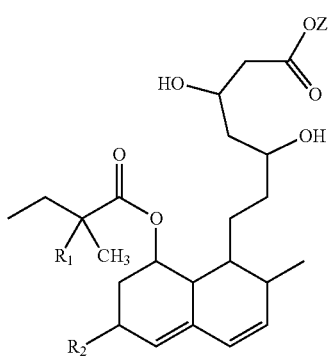

II wherein Z represents H, ammonium, or a metal cation,
R$_1$ is H or C$_1$-C$_6$ alkyl, preferably H or CH$_3$,
R$_2$ is CH$_3$, OH, CH$_2$OH, CH$_2$OC(O)R$_3$, CH$_2$OR$_3$, or COOR$_4$, preferably CH$_3$ or OH,
R$_3$ and R$_4$ are independently selected from the group consisting of H and C$_1$-C$_6$ alkyl.

In another aspect, the present invention provides a method for preparing a compound of formula I, comprising the following steps: (1) lactonizing a compound of formula II into a compound of formula I in the presence of a catalyst selected from the group consisting of organic sulfonic acid, monohalo or polyhalo acetic acid and a mixture thereof and a dehydrant in a first solvent, wherein the lactonization of the compound of formula II is not required to be carried out under heat, the lactone compound of formula I is obtained by filtering to remove the dehydrant from the first solvent, evaporating the first solvent and isolating; (2) crystallizing the lactone product in a second solvent;

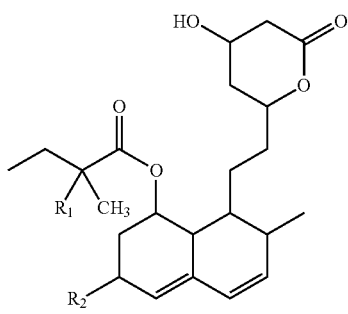

I

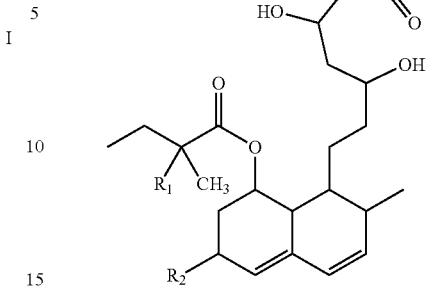

II wherein Z represents H, ammonium, or a metal cation,
R$_1$ is H or CH$_3$,
R$_2$ is CH$_3$.

The method for preparing a statin compound by lactonization of the present invention may be carried out at ambient temperature. In addition, the reaction time is short, post-processing is convenient, and there is no strict requirements for the reaction agents, reaction devices and operations. Accordingly, the method is convenient to carry out and is suitable for the industrial mass production. In addition, the method for preparing a statin compound by lactonization of the present invention can give a statin compound with high purity in a high yield.

DETAILED DESCRIPTION OF THE INVENTION

One embodiment of the method for preparing a statin compound by lactonization of the present invention comprises lactonizing a compound of formula II into a compound of formula I in the presence of a strong acid catalyst and a dehydrant in a first solvent,

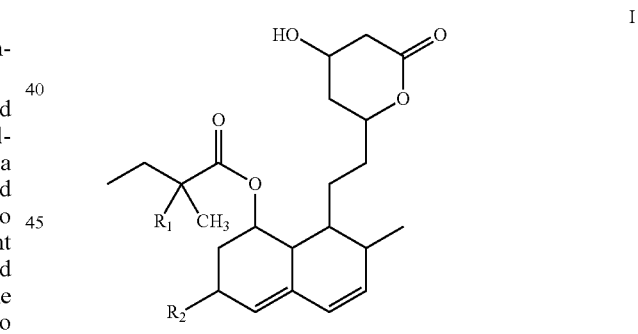

I

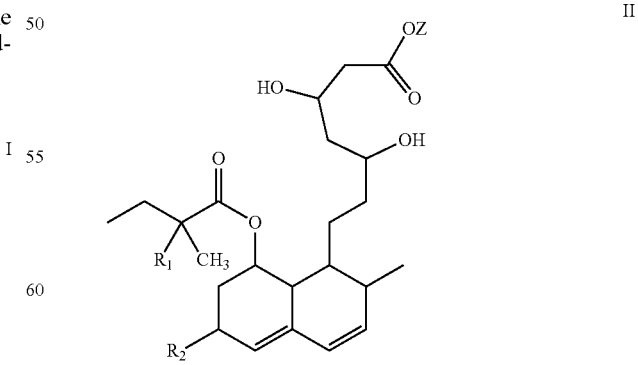

II wherein Z represents H, ammonium, or a metal cation,
R$_1$ is H or C$_1$-C$_6$ alkyl, preferably H or CH$_3$,
R$_2$ is CH$_3$, OH, CH$_2$OH, CH$_2$OC(O)R$_3$, CH$_2$OR$_3$, or COOR$_4$, preferably CH$_3$ or OH, $R_3$ and $R_4$ are independently selected from the group consisting of H and $C_1$-$C_6$ alkyl.

In the above compound of formula II, the metal cation can be an alkali metal cation such as sodium or potassium, or alkaline earth metal cation such as calcium or magnesium, preferably alkali metal cation, alkaline earth metal cation or aluminium cation, more preferably sodium ion, potassium ion, calcium ion, or aluminium ion.

During lactonization of the dihydroxy acid, when Z is ammonium or a metal cation, ammonium or the metal cation in the compound of formula II is first neutralized into an ammonium or metal salt of a strong acid by the strong acid catalyst to form a free dihydroxy acid, which is then subjected to catalytical dehydration and forms a lactone by a ring closure reaction. As a result, the strong acid catalyst acts as both a neutralizing agent and a catalyst (for example, simvastatin ammonium salt and organic sulfonic acid).

The molar ratio of the strong acid catalyst as used in the present invention to the compound of formula II can be 1.01-1.05:1. Preferably, the molar ratio of the organic sulfonic acid or α-monohalo or polyhalo acetic acid to the compound of formula II can be 1.01-1.05:1.

In the method for preparing the statin compound by lactonization of the present invention, since the dehydrant is used to remove water generated during the lactonization of the compound of formula II into the compound of formula I to shift the equilibrium toward the formation of lactone, the reaction is carried out more completely, the reaction time is shortened, the production of byproduct dimers is decreased, and the yield and purity of products are increased.

The dehydrant as used in the present invention is also called a drier, and can include, but are not limited to, magnesium sulfate, sodium sulfate, calcium chloride, molecular sieve, silica-gel drier, montmorillonite drier, active mineral drier,

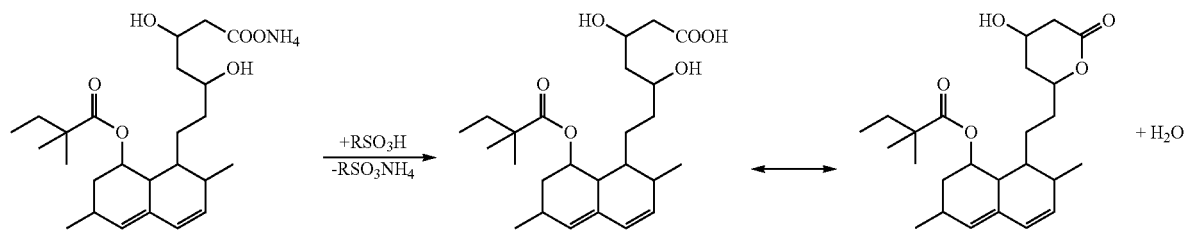

Accordingly, the strong acid catalyst as used in the present invention can be an inorganic or organic acid, provided that the acidity thereof is sufficient to catalyze the formation of lactone. Examples of suitable strong acid catalysts can include, but are not limited to, sulphuric acid, hydrochloric acid, hydrobromic acid, phosphoric acid, organic sulfonic acid, formic acid, α-monohalo or polyhalo $C_1$-$C_8$ alkyl carboxylic acid and a mixture of two or more of the above-mentioned substances, in which the halogen atom is fluorine, chlorine, or bromine, preferably fluorine or chlorine. Examples of organic sulfonic acids can include, but are not limited to, methanesulfonic acid, ethanesulfonic acid, p-toluenesulfonic acid, and benzenesulfonic acid, preferably p-toluenesulfonic acid. The α-monohalo or polyhalo $C_1$-$C_8$ alkyl carboxylic acid can be preferably α-monohalo or polyhalo $C_1$-$C_4$ alkyl carboxylic acid, more preferably α-monohalo or polyhalo acetic acid, in which the halogen atom is fluorine, chlorine, or bromine, preferably fluorine or chlorine. Examples of α-monohalo or polyhalo acetic acids can include, but are not limited to, trifluoroacetic acid, trichloroacetic acid, chloroacetic acid, and dichloroacetic acid, preferably trifluoroacetic acid.

The strong acid catalyst as used in the present invention can be preferably sulphuric acid, hydrochloric acid, phosphoric acid, organic sulfonic acid, formic acid, α-monohalo or polyhalo $C_1$-$C_4$ alkyl carboxylic acid or a mixture of two or more of the above-mentioned substances, more preferably organic sulfonic acid, α-monohalo or polyhalo acetic acid or a mixture thereof, even more preferably methanesulfonic acid, ethanesulfonic acid, p-toluenesulfonic acid, benzenesulfonic acid, α-monohalo or polyhalo acetic acid or a mixture of two or more of the above-mentioned substances, most preferably methanesulfonic acid, p-toluenesulfonic acid, benzenesulfonic acid, trifluoroacetic acid, chloroacetic acid, trichloroacetic acid, or a mixture of two or more of the above-mentioned substances.

and calcium sulfate; preferably magnesium sulfate, sodium sulfate, calcium chloride and molecular sieve; more preferably magnesium sulfate; most preferably anhydrous magnesium sulfate.

In the method of the present invention, the molar ratio of the dehydrant to the compound of formula II can be 0.5-2:1. Preferably, the molar ratio of anhydrous magnesium sulfate to the compound of formula II can be 0.5-2:1.

In the method of the present invention, the first solvent, i.e. reaction medium or reaction solvent, can be any inert organic solvent, provided that the compound of formula I as obtained can be sufficiently dissolved therein. Moreover, the dehydrant can be removed from the reaction medium by a simple reaction operation such as filtration after the lactonization is finished.

The first solvent is preferably an inert, water immiscible organic solvent, such as alkanes, cycloalkanes, arenes, haloalkanes, or esters, or a mixture of two or more of the above-mentioned substances, more preferably an anhydrous, inert and water immiscible organic solvent. Examples of the alkanes solvent can include, but are not limited to, n-pentane, n-hexane and the like; examples of the cycloalkanes solvent can include, but are not limited to, cyclopentane, cyclohexane and the like; examples of the arenes solvent can include, but are not limited to, benzene, toluene, xylene, and the like; examples of the haloalkanes can include, but are not limited to, dichloromethane, dichloroethane, chloroform, and the like; examples of the esters solvent can include, but are not limited to, ethyl acetate, isopropyl acetate, and the like. The above solvents can be used alone, or two or more solvents can be used in combination in any ratio in the method of the present invention. The above solvents can be easily recovered by distillation, which decreases the reaction cost. Preferably, dichloromethane is used as the first solvent.

In the method of the present invention, since the dehydrant is used to remove water generated during the lactonization, the selection scopes of strong acid catalyst and the first solvent are broadened. In the method of the present invention, both anhydrous strong acid catalyst and strong acid catalyst containing crystal water can be used; the first solvent, the compound of formula II, and strong acid catalyst do not need non-aqueous processing; the moisture in the air is not required to be isolated by a drying tube in the atmosphere of nitrogen, which simplify the requirements for reaction agents, reaction catalysts, reaction mediums, reaction devices and reaction operations.

The lactonization can be carried out at ambient temperature, preferably 10° C.-30° C., more preferably 15° C.-20° C. The reaction time depends on the amount and acidity of the strong acid catalyst, and is generally within 2 hours, preferably 1-1.5 hours.

In another embodiment of the method for preparing a statin compound by lactonization in the present invention, the method further comprises the following steps: removing the dehydrant and the first solvent after the compound of formula II is lactonized into the compound of formula I, and then crystallizing the resultant product in a second solvent to obtain the compound of formula I.

After the lactonization is finished, calculated amount of base (such as $NH_4HCO_3$, $NaHCO_3$, $KHCO_3$, $(NH_4)_2CO_3$, $Na_2CO_3$, $K_2CO_3$ and other common used weak bases) can be firstly used to neutralize excess strong acid, and then the dehydrant is removed, for example by filtration. Alternatively, after the reaction is finished, the reaction mixture can be extracted with saturated or unsaturated weak base aqueous solution. As a result, the resultant aqueous phase contains water-soluble ammonium or metal salt, and the organic phase contains the lactone as obtained. Subsequently, the solvent in the organic phase is removed by distillation or other methods to obtain the lactone product.

Therefore, in the method for preparing the statin compound by lactonization in the present invention, the crude product of the compound of formula I is obtained by merely removing dehydrant (such as by filtration) and reaction solvents (such as by distillation), which simplifies the procedure and time of post-processing, and thus the method of the present invention is easier to carry out and is appropriate for industrial mass production.

The lactone product can be purified by suitable purifying methods, such as crystallization and the like, to obtain the desired purity. The second solvent, i.e. crystallization solvent, can be a single or mixed solvent. The second solvent can be water, alcohols, alkanes, cycloalkanes, arenes, esters, nitriles, ketones, haloalkanes, or a mixture of two or more of the above-mentioned substances. Examples of the second solvent can include, but are not limited to, water, methanol, ethanol, n-hexane, cyclohexane, benzene, toluene, ethyl acetate, isopropyl acetate, acetonitrile, acetone, dichloromethane, dichloroethane, chloroform or a mixture of two or more of the above-mentioned substances, preferably a mixed solvent of methanol/ethanol and water, or a mixed solvent of toluene and cyclohexane.

When the crystallization solvent is preferably a mixed solvent of ethanol and water, or a mixed solvent of toluene and cyclohexane, based on 1 g of the compound of formula II, a mixed solvent of 8-10 ml of water and 8-10 ml of ethanol, or a mixed solvent of 2-3 ml of toluene and 19-21 ml of cyclohexane can be used.

In the method of the present invention, the compound of formula I can be crystallized at 10° C.-50° C. Preferably, the compound of formula I can be crystallized in a mixed solvent of ethanol/water or toluene/cyclohexane at 10° C.-50° C.

It should be understood by a person skilled in the art that the second solvent used during the crystallization of the compound of formula I is not limited to the specific solvents as listed above. Any suitable single or mixed solvent can be used as the crystallization solvent according to the disclosure of the present invention in view of common technical means in the art, provided that the compound of formula I is soluble in the single solvent, while the impurities such as dimers are slightly soluble or insoluble in the single solvent, or the compound of formula I is soluble in one of the mixed solvent and less soluble in the other one of the mixed solvent.

It should also be understood by a person skilled in the art that the ratio of the second solvent used during the crystallization of the compound of formula I to the compound of formula II is not limited to the above ratio. The suitable ratio of the second solvent to the compound of formula II can be selected according to the selected type of the second solvent.

In addition, it should also be understood by a person skilled in the art that the crystallization temperature during the crystallization of the compound of formula I is not limited to the above temperature range. The suitable crystallization temperature can be selected according to the selected type of the second solvent.

In another embodiment of the method for preparing a statin compound by lactonization of the present invention, the method further comprises the following steps: removing the dehydrant and the first solvent after the compound of formula II is lactonized into the compound of formula I; adding a third solvent to dissolve the resultant residue under heat, cooling down, crystallizing, and filtering to obtain the compound of formula I; and then recrystallizing the compound of formula I in the second solvent to obtain the compound of formula I with higher purity.

The third solvent can be organic solvents such as alkane, cycloalkane, arene, ester, haloalkane, or a mixture of two or more of the above-mentioned substances, provided that the compound of formula I is soluble therein, while impurities such as dimers are slightly soluble or insoluble therein. The third solvent can preferably be n-hexane, cyclohexane, benzene, toluene, ethyl acetate, isopropyl acetate, dichloroethane, chloroform, or a mixture of two or more of the above-mentioned substances, more preferably cyclohexane.

In another embodiment of the method for preparing the statin compound by lactonization of the present invention, the method comprises the following steps: (1) lactonizing a compound of formula II into a compound of formula I in the presence of a catalyst selected from the group consisting of organic sulfonic acid, monohalo or polyhalo acetic acid and a mixture thereof and a dehydrant in a first solvent, wherein the lactonization of the compound of formula II is not required to be carried out under heat, and the lactone compound of formula I is obtained by filtering to remove the dehydrant from the first solvent, evaporating the first solvent and isolating; (2) crystallizing the lactone product in a second solvent;

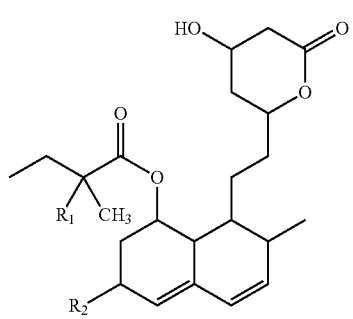

I

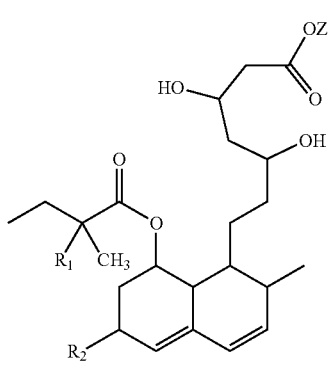

II wherein Z represents H, ammonium, or a metal cation,
R₁ is H or CH₃,
R₂ is CH₃.

In the embodiment, the organic sulfonic acid is anhydrous or contains crystal water, and can be selected from the group consisting of methanesulfonic acid, p-toluenesulfonic acid, benzenesulfonic acid, and a mixture of two or more of the above-mentioned substances, preferably p-toluenesulfonic acid; haloacetic acid can be selected from the group consisting of trifluoroacetic acid, chloroacetic acid and dichloroacetic acid, preferably trifluoroacetic acid. The molar ratio of the catalyst, organic sulfonic acid or haloacetic acid, to the compound of formula II can be 1.01-1.05:1.

The dehydrant can be magnesium sulfate, sodium sulfate, calcium chloride, molecular sieve, and the like, preferably anhydrous magnesium sulfate. The molar ratio of the dehydrant to the compound of formula II can be 0.5-2:1.

The first solvent can preferably be an inert solvent, preferably an inert and water immiscible solvent, more preferably an anhydrous, inert and water immiscible solvent. The first solvent can be arene such as benzene, toluene; or chloroalkane such as dichloromethane, dichloroethane, chloroform; or ethyl acetate, isopropyl acetate; or a mixture of two or more of the above-mentioned substances in any ratio; preferably dichloromethane.

The lactonization is substantially carried out at ambient temperature. The reaction time depends on the amount and activity of the acid, and is generally within 2 hours, preferably 1-1.5 hours.

The crystallization solvent can be water, methanol, ethanol, n-hexane, cyclohexane, ethyl acetate, isopropyl acetate, acetonitrile, acetone, toluene, dichloroethane, chloroform or a mixed solvent of two or more of the above-mentioned substances, preferably a mixed solvent of ethanol and water, or a mixed solvent of toluene and cyclohexane.

When the crystallization solvent is preferably a mixed solvent of ethanol and water, or a mixed solvent of toluene and cyclohexane, based on 1 g of the compound of formula II, a mixed solvent of 8-10 ml of water and 8-10 ml of ethanol or a mixed solvent of 2-3 ml of toluene and 19-21 ml of cyclohexane can be used.

The compound of formula I can be crystallized at 10° C.-50° C. Preferably, the compound of formula I can be crystallized in a mixed solvent of ethanol/water or toluene/cyclohexane at 10° C.-50° C.

The method for preparing the statin compound by lactonization of the present invention allows completion of the lactonization reaction at ambient temperature, shortens reaction time, simplifies the post-processing operations and the strict requirements for reaction agents, reaction devices and reaction operations, facilitates industrial large-scale implementation, and is a safe and effective industrial production method. The quality of the statin compound prepared by the method of the present invention, especially simvastatin, complies with the EP, USP pharmacopoeia standards or customer requirements.

Embodiments

EXAMPLE 1

100 g of simvastatin ammonium salt, 800 ml of dichloromethane, 43.2 g of p-toluenesulfonic acid monohydrate, and 20 g of anhydrous magnesium sulfate were added to a 1 L reaction flask, and the reaction mixture was allowed to stir at 15~20° C. until the end of the reaction. A TLC monitoring was carried out at the end of the reaction. Subsequently, 0.6 g of sodium bicarbonate and 10 g of active carbon were added to the reaction mixture, which was then stirred for 30 min and then filtered. The filter cake was washed with dichloromethane. The solvent was distilled off under ordinary pressure at 45° C., and the residual solvent was pumped under reduced pressure. 800 ml of cyclohexane was added to the residue. The mixture was heated to 50° C., stirred uniformly, placed, cooled down, crystallized, filtered, and the filter cake was dried for 1 h at 50° C. to give a crude product.

The crude product was heat-dissolved with 700 ml of ethanol. The mixture was decolored with 5 g of active carbon for 30 min and then filtered. The filter cake was washed with 100 ml of ethanol. The filtrate was heated to 50° C., and then 800 ml of deionized water was added. The solution was gradually cooled down to 10° C., crystallized, and filtered after 2 h. The filter cake was washed with 100 ml of ethanol:water (1:1), and dried to give simvastatin 83.1 g, with a yield of 90.08%, in which a content of simvastatin was 99.45%, and a content of a dimmer thereof was 0.09% (HPLC).

EXAMPLE 2

100 g of simvastatin ammonium salt, 800 ml of dichloromethane, 42 g of benzenesulfonic acid with 1.5 H₂O, and 40 g of anhydrous magnesium sulfate were added to a 1 L reaction flask, and the reaction mixture was allowed to stir at 15 ~20° C. until the end of reaction. A TLC monitoring was carried out at the end of the reaction. Subsequently, 0.6 g of sodium bicarbonate and 10 g of active carbon were added to the reaction mixture, which was then stirred for 30 min and filtered. The filter cake was washed with dichloromethane. The solvent was evaporated under ordinary pressure at 45° C., and the residual solvent was pumped under reduced pressure. 800 ml of cyclohexane was added to the residue. The mixture was heated to 50° C., stirred uniformly, placed, cooled down, crystallized, and filtered. The filter cake was dried for 1 h at 50° C. to give a crude product.

The crude product was heat-dissolved with 700 ml of ethanol. The mixture was decolored with 5 g of active carbon for 30 min, filtered, and the filter cake was washed with 100 ml of ethanol. The filtrate was heated to 50° C., and then 800 ml of deionized water was added. The solution was gradually cooled down to 10° C., crystallized, and filtered after 2 h. The filter cake was washed with 100 ml of ethanol:water (1:1), and dried to give simvastatin 81.9 g with a yield of 88.78%, in which a content of simvastatin was 99.36%, and a content of a dimmer thereof was 0.12%.

EXAMPLE 3

100 g of simvastatin ammonium salt, 600 ml of chloroform, and 15 g of anhydrous magnesium sulfate were added to a 1 L reaction flask, and a solution of 21.9 g of methanesulfonic acid in 200 ml of chloroform was dropwise added at 15~20° C. within 30~50 min, and the mixture was allowed to continue reacting at 15~20° C. until the end of reaction. A TLC monitoring was carried out at the end of the reaction. Subsequently, 0.6 g of sodium bicarbonate and 10 g of active carbon were added to the reaction mixture, which was then stirred for 30 min and filtered. The filter cake was washed with chloroform which was then evaporated under reduced pressure to dryness. After that, 800 ml of cyclohexane was added to the residue. The mixture was heated to 50° C., stirred uniformly, placed, cooled down, crystallized, and filtered. The filter cake was dried for 1 h to give a crude product.

The crude product was heat-dissolved with 700 ml of ethanol. The mixture was decolored with 5 g of active carbon for 30 min, filtered, and the filter cake was washed with 100 ml of ethanol. 800 ml of deionized water was added to the filtrate. The solution was heated to 50° C., gradually cooled down to 10° C., and filtered after crystallization was completed. The filter cake was washed with 100 ml of ethanol:water (1:1), and dried to give simvastatin 81.5 g with a yield of 88.33%, in which a content of simvastatin was 99.38%, and a content of a dimmer thereof was 0.10%.

EXAMPLE 4

100 g of simvastatin ammonium salt, 800 ml of chloroform, 43.2 g of p-toluenesulfonic acid monohydrate, and 20 g of anhydrous magnesium sulfate were added to a 1 L reaction flask, and the reaction mixture were allowed to stir at 15~20° C. until the end of reaction. A TLC monitoring was carried out at the end of the reaction. Subsequently, simvastatin 80.2 g was obtained by the same procedure as described in example 3 with a yield of 86.93%, in which a content of simvastatin was 99.48%, and a content of a dimmer thereof was 0.14%.

EXAMPLE 5

100 g of simvastatin ammonium salt, 600 ml of dichloromethane, and 15 g of anhydrous magnesium sulfate were added to a 1 L reaction flask, and a solution of 25.9 g of trifluoroacetic acid in 200 ml of dichloromethane was dropwise added at 15~20° C. within 30-50 min. The mixture was allowed to continue reacting at 15~20° C. until the end of reaction. A TLC monitoring was carried out at the end of the reaction. Subsequently, 0.6 g of sodium bicarbonate and 10 g of active carbon were added to the reaction mixture, which was then stirred for 30 min, filtered, and the filter cake was washed with dichloromethane. The solvent was evaporated under ordinary pressure at 45° C., and the residual solvent was pumped under reduced pressure. 800 ml of cyclohexane was added to the residue. The mixture was heated to 50° C., stirred uniformly, placed, cooled down, crystallized, and filtered. The filter cake was dried to give a crude product.

After the crude product was heat-dissolved with 700 ml of ethanol, 5 g of active carbon was added. The mixture was stirred for 30 min and then filtered. The filter cake was washed with 100 ml of ethanol. 800 ml of deionized water was then added to the filtrate. The solution was heated to 50° C., stirred uniformly, gradually cooled down to 10° C., and filtered after crystallization was completed. The filter cake was washed with 100 ml of ethanol: water (1:1), and then dried to give simvastatin 80.9 g with a yield of 87.69%, in which a content of simvastatin was 99.52%, and a content of a dimmer thereof was of 0.07%.

EXAMPLE 6

100 g of simvastatin ammonium salt, 600 ml of dichloromethane, and 15 g of anhydrous magnesium sulfate were added to a 1 L reaction flask, and a solution of 29.3 g of dichloroacetic acid in 200 ml of dichloromethane was dropwise added at 15~20° C. within 30-50 min, and the reaction mixture was allowed to continue reacting at 15~20° C. until the end of reaction. A TLC monitoring was carried out at the end of the reaction. Subsequently, 80.3 g of simvastatin was obtained by the same procedure as described in example 5 with a yield of 87.04%, in which a content of simvastatin was 99.4%, and a content of a dimmer thereof was 0.06%.

EXAMPLE 7

100 g of simvastatin ammonium salt, 800 ml of dichloromethane, 21.5 g of chloroacetic acid, and 15 g of anhydrous magnesium sulfate were added to a 1 L reaction flask, and the reaction mixture was allowed to stir at ambient temperature until the end of reaction. A TLC monitoring was carried out at the end of the reaction. Subsequently, 79.2 g of simvastatin was obtained by the same procedure as described in example 5 with a yield of 85.85%, in which a content of simvastatin was 99.22%, and a content of a dimmer thereof was 0.13%.

The invention claimed is:

1. A method for preparing a compound of formula I, comprising lactonizing a compound of formula II into the compound of formula I in the presence of a strong acid catalyst and a dehydrant in a first solvent,

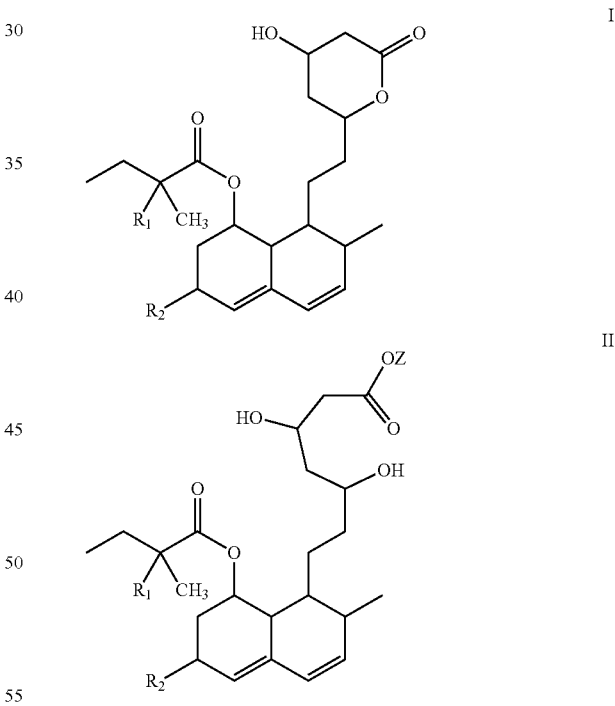

wherein Z represents ammonium,
$R_1$ is H or $C_1$-$C_6$ alkyl,
$R_2$ is $CH_3$,
$R_3$ and $R_4$ are independently selected from the group consisting of H and $C_1$-$C_6$ alkyl, and
wherein the dehydrant is magnesium sulfate.

2. The method of claim 1, wherein a molar ratio of the strong acid catalyst to the compound of formula II is 1.01-1.05:1.

3. The method of claim 1, wherein a molar ratio of the dehydrant to the compound of formula II is 0.5-2:1.

4. The method of claim 1, wherein the strong acid catalyst is selected from the group consisting of sulphuric acid, hydrochloric acid, hydrobromic acid, phosphoric acid, organic sulfonic acid, formic acid, α-monohalo or polyhalo $C_1$-$C_8$ alkyl carboxylic acid and a mixture of two or more of the above-mentioned substances, wherein the halogen atom is fluorine, chlorine, or bromine.

5. The method of claim 1, wherein the first solvent is an inert and water immiscible organic solvent.

6. The method of claim 1, wherein a reaction temperature is an ambient temperature.

7. The method of claim 1, wherein a reaction time is 2 hours.

8. The method of claim 1, further comprising the following steps: removing the dehydrant and the first solvent after the compound of formula II is lactonized into the compound of formula I, and then crystallizing the resultant product in a second solvent to obtain the compound of formula I, wherein the second solvent is selected from the group consisting of alcohols, a mixture of water and alcohols, a mixture of n-hexane and arenes, cyclohexane, a mixture of cyclohexane and arenas, a mixture of esters and n-hexane, a mixture of esters and cyclohexane, a mixture of acetonitrile and water, ketones, and a mixture of ketones and water.

9. The method of claim 8, wherein the second solvent is selected from the group consisting of methanol, ethanol, a mixture of water and methanol, a mixture of water and ethanol, a mixture of n-hexane and benzene, a mixture of n-hexane and toluene, cyclohexane, a mixture of cyclohexane and benzene, a mixture of cyclohexane and toluene, a mixture of ethyl acetate and n-hexane, a mixture of isopropyl acetate and n-hexane, a mixture of propyl acetate and n-hexane, a mixture of ethyl acetate and cyclohexane, a mixture of isopropyl acetate and cyclohexane, a mixture of propyl acetate and cyclohexane, a mixture of acetonitrile and water, acetone, butanone, a mixture of acetone and water, and a mixture of butanone and water.

10. The method of claim 9, wherein based on 1 g of the compound of formula II, a mixed solvent of 8-10 ml of water and 8-10 ml of ethanol or a mixed solvent of 2-3 ml of toluene and 19-21 ml of cyclohexane is used.

11. The method of claim 8, wherein the crystallization is carried out at a temperature of 10° C.-50° C.

12. The method of claim 8, further comprising the following steps: after removing the first solvent and before carrying out the crystallization in the second solvent, adding a third solvent to dissolve a residue as obtained after removing the first solvent under heat, cooling down, crystallizing, and filtering to obtain the compound of formula I.

13. The method of claim 12, wherein the third solvent is selected from the group consisting of alkanes, cycloalkanes, arenes, esters, haloalkanes, and a mixture of two or more of the above-mentioned substances.

14. The method of claim 1, wherein $R_1$ is H or $CH_3$.

15. The method of claim 4, wherein the halogen atom is fluorine or chlorine.

16. The method of claim 4, wherein the strong acid catalyst is selected from the group consisting of sulphuric acid, hydrochloric acid, phosphoric acid, organic sulfonic acid, formic acid, α-monohalo or polyhalo $C_1$-$C_4$ alkyl carboxylic acid and a mixture of two or more of the above-mentioned substances.

17. The method of claim 4, wherein the strong acid catalyst is selected from the group consisting of organic sulfonic acid, monohalo or polyhalo acetic acid and a mixture thereof.

18. The method of claim 4, wherein the strong acid catalyst is selected from the group consisting of methanesulfonic acid, ethanesulfonic acid, p-toluenesulfonic acid, benzenesulfonic acid, monohalo or polyhalo acetic acid and a mixture of two or more of the above-mentioned substances.

19. The method of claim 4, wherein the strong acid catalyst is selected from the group consisting of methanesulfonic acid, p-toluenesulfonic acid, benzenesulfonic acid, trifluoroacetic acid, chloroacetic acid, trichloroacetic acid and a mixture of two or more of the above-mentioned substances.

20. The method of claim 5, wherein the first solvent is selected from the group consisting of alkanes, cycloalkanes, arenes, haloalkanes, esters and a mixture of two or more of the above-mentioned substances.

21. The method of claim 5, wherein the first solvent is selected from the group consisting of n-hexane, cyclohexane, benzene, toluene, dichloromethane, dichloroethane, chloroform, ethyl acetate, isopropyl acetate and a mixture of two or more of the above-mentioned substances.

22. The method of claim 6, wherein the reaction temperature is 10° C.-30° C.

23. The method of claim 6, wherein the reaction temperature is 15° C.-20° C.

24. The method of claim 7, wherein the reaction time is 1-1.5 hours.

25. The method of claim 9, wherein the second solvent is selected from the group consisting of a mixture of water and methanol, a mixture of water and ethanol, a mixture of cyclohexane and toluene, a mixture of acetone and water, and a mixture of butanone and water.

26. The method of claim 13, wherein the third solvent is selected from the group consisting of n-hexane, cyclohexane, benzene, toluene, ethyl acetate, isopropyl acetate, dichloroethane, chloroform, and a mixture of two or more of the above-mentioned substances.

27. The method of claim 13, wherein the third solvent is cyclohexane.

* * * * *